United States Patent [19]

Barnard et al.

[11] 3,938,253

[45] Feb. 17, 1976

[54] DENTAL INSTRUMENT HOLDER

[75] Inventors: John David William Barnard, East Grinstead; Peter Frank Kurer, Cheadle, both of England

[73] Assignee: Kurer Research & Development, England

[22] Filed: Oct. 1, 1974

[21] Appl. No.: 511,068

[30] Foreign Application Priority Data
Oct. 9, 1973  United Kingdom............... 47071/73

[52] U.S. Cl.................................. 32/40 R; 32/57
[51] Int. Cl.² ........................................ A61C 3/00
[58] Field of Search .............................. 32/40 R:57

[56] References Cited
UNITED STATES PATENTS
3,295,208   1/1967   Redtenbacher.................... 32/40 R

*Primary Examiner*—Robert Peshock
*Attorney, Agent, or Firm*—Wolf, Greenfield & Sacks

[57] ABSTRACT

A holder for receiving dental root canal instruments consists of two circular plates arranged in coaxial spaced-apart disposition, one plate having a series of through holes therein each to receive a respective instrument with the tip thereof resting on the other plate the separation of the two plates, and thus the distance between that plate face which receives an instrument tip and the corresponding face of the other plate, being selectively adjustable to provide a datum for setting indicators on the respective instruments mounted on the holder.

3 Claims, 3 Drawing Figures

DENTAL INSTRUMENT HOLDER

The present invention relates to holders for dental root-canal instruments such as reamers, broaches, silver points, and files.

When the pulp of a tooth becomes infected, it is common practice to drill through the crown of the tooth, remove the pulp right down to the tip of the root canal, and plug the root canal before filling the tooth. The pulp is removed using reamers or files. It is important to determine the length of root canal instrument to be used in treating the tooth, since if it is too long the bone may be damaged, and if it is too short the root canal may remain untreated near its tip.

The required length of instrument is found by measuring the length of a wire instrument inserted into the root canal up to the tip of the root, as indicated on an X-ray photograph. The root canal instruments to be used are then selected and the required length is measured off on each and marked by a marking disc threaded onto each instrument. This is clearly a time consuming process, in which there is some risk of error.

The present invention provides a length-determining holder for dental root canal instruments, comprising a base plate on which the tips of the instruments are to rest, and a holding plate parallel to the base plate, the holding plate having through bores for holding the instruments, the required length of the instruments being determined by the distance between the upper surface of the base plate and the upper surface of the holding plate, the plates being guided for movement towards and away from each other.

In use, the holder holds one or more sets of instruments (of various sizes), the instruments being held in the respective bores of the holding plate, each instrument carries a marker which is movable along the instrument to abut against the upper surface of the holding plate and indicate the required length. The instrument can be stored in the holder and can be sterilized with the holder.

Preferably the holder includes a scale readable in association with the upper surface of the holding plate or base plate and indicating the distance between the said surfaces. The plates may conveniently be moved by a screw, one revolution of the screw producing a displacement which is a known subdivision of the scale, in the manner of a micrometer screw, or any other suitable method.

The invention will now be described further, by way of example only, with reference to the accompanying drawings, in which.

Figure 1:
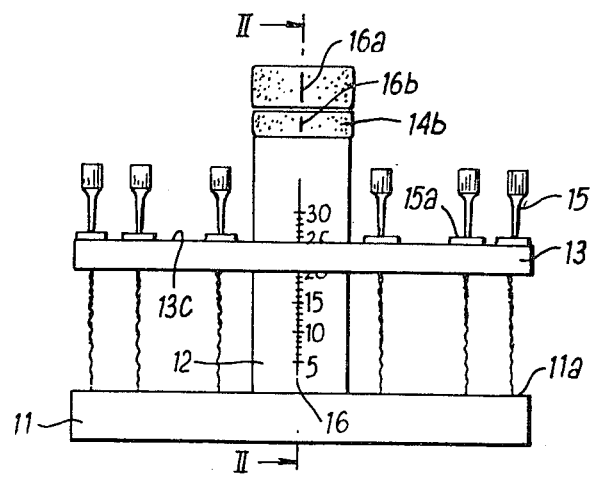
FIG. 1 is a side elevation of a first form of holder constructed in accordance with the invention, there being a set of reamers in position thereon.
Figure 2:
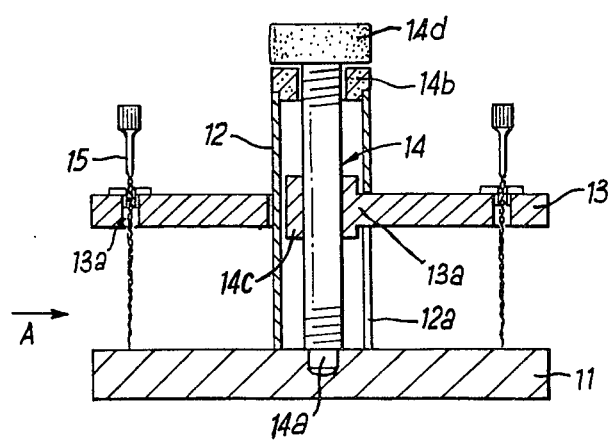
FIG. 2 is a section on line II—II of FIG. 1.

Referring now to the drawings, and particularly to FIGS. 1 and 2 thereof, a holder for dental instruments such as reamers comprises a circular base plate 11, a hollow pillar 12 secured coaxially of such base plate and extending upwardly therefrom, a holding plate 13 arranged in spaced parallel disposition relative to the base plate and slidable longitudinally of the pillar, and an adjustment means 14 for supporting the holding plate 13 relative to the base plate 11 and adapted, upon actuation, to adjust the relative position of the base plate 11 and holding plate 13 in the axial direction of the pillar 12.

The holding plate 13 is of circular form and of a like diameter to the base plate 11, being arranged coaxially therewith and has a series of twelve through holes 13a therein arranged at equal centres peripherally of the holding plate and at a common distance from the centre of such plate.

The adjustment means 14 comprises a screw-threaded rod 14a of 1 mm. pitch disposed within the pillar and captively engaged with a plug 14b at the upper end of such pillar and a nut 14c engaged with the said rod and secured to a radially inwardly directed extension 13b the holding plate 13, the said extension 13a passing through a longitudinal slot 12a in the wall of the pillar 12. The upper end of the rod 14a carries a knurled knob 14d, and such rod is freely rotatable in but axially fixed relative to the plug. Rotation of the nut 14c is precluded by co-operation between the extension 13b to the holding plate 13 and the lateral edges of the slot 12a in the pillar.

A reamer 15 is positioned in each of the through holes 13a the tips of such reamers resting on the upper surface 11a of the base plate 11 and the reamers being arranged circumferentially in order of size (diameter).

The distance between the upper surface 13c of the holding plate and the corresponding surface of the base plate represents the required length of the reamers as determined by clinical methods of a conventional kind, such length being set on the individual reamers by movement of a disc 15a of plastics or rubber along each reamer into abutment with the surface of the holding plate.

As will readily be apparent, the structure as aforesaid will provide a convenient means for setting the working length of a reamer by reference to a datum as determined by conventional clinical methods, the holding plate being appropriately positioned relative to the base plate by rotation of the rod of the adjustment means to give the datum, the reamers being engaged with respective ones of the through holes, and the discs being moved axially of the reamers and into contact with the upper surface of the holding plate.

For a different datum, the holding plate is moved to a corresponding position relative to the base plate, and the reamers, or other instruments, set as before.

If desired, the pillar may have a linear scale 16 marked thereon to facilitate the ready reproduction of a datum of known magnitude, the scale being read off against the plane of the top surface of the holding plate and such reading being facilitated if desired, by the provision of co-operating index marks 16a, 16b on the knob and plug.

Figure 3:
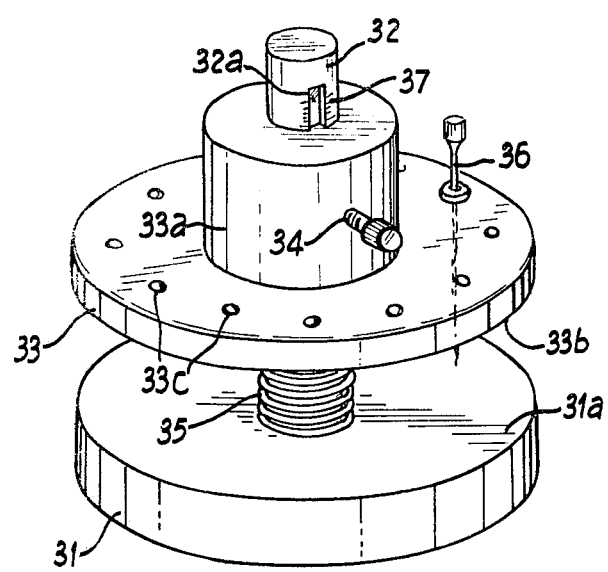
FIG. 3 is a perspective view of a second form of holder.

A second and simplified embodiment is shown in FIG. 3 and comprises a base plate 31, a pillar 32 extending upwardly from the base plate, a holding plate 33 slidable axially of the pillar 32, and a locking screw 34 extending through a threaded radial bore in a boss 33a formed integrally with the holding plate, the said screw 34 engaging a channel 32a provided in the pillar and extending longitudinally thereof.

A cushioning spring 35 is provided between the upper surface 31a of the base plate and the underside 33b of the holding plate, such spring being arranged coaxially with the pillar 32.

As in the case of the embodiment of FIGS. 1 and 2, the holding plate includes a series of through holes 33c each to receive a respective reamer 36, or other dental instrument, the said holes being equi-spaced and lying on a circle concentric with the holding plate.

A linear scale 37 is provided on the pillar and conveniently at the lateral edges of the channel 32a, the said scale being read in conjunction with the upper surface 31a of the holding plate.

The diameter of the locking screw 34 corresponds closely with the width of the channel 32a so as positively to locate the holding plate in the peripheral direction thereof.

The embodiment of FIG. 3 is used in like manner to that of FIGS. 1 and 2 except as regards the manner of adjustment and thus further description thereof is thought unnecessary.

It will be seen that the required length for the reamers can be determined quickly and accurately for the whole set of reamers, which are already arranged in the correct order of size (diameter). The reamers can be stored in the holder and sterilized in the holder, so that they need never become disarranged.

Various modifications may be made within the scope of the invention. For instance, more than one circle of through bores can be provided, to accommodate other instruments. In the case of the embodiment of FIGS. 1 and 2, one or more further guide columns could be provided, separate from the screw, so as to simplify the arrangement of the screw, whilst in the case of the arrangement of FIG. 3, an alternative cushioning means to that shown, for example a friction pad on the inner end of the screw, may be used.

What we claim is:

1. A dental instrument holder for determining the working length for dental root canal instruments comprising
   1. a base plate having a flat upper surface forming a datum plane,
   2. a post extending upwardly from the base plate,
   3. a holding plate having a flat upper surface, the holding plate having an aperture in which the post is received in a manner maintaining the flat upper surface of the holding plate parallel to the datum plane, the flat upper surface of the holding plate having a plurality of spaced parallel apertures extending through the holding plate in which dental root canal instruments can be received, the working length of the instruments being determined by the distance between the datum plane and the flat upper surface of the holding plate,
   4. resilient means disposed around the post and acting between the base plate and the holding plate to resiliently support the holding plate for sliding movement on the post, and
   5. means for locking the holding plate to the post at a selected level relative to the datum plane.

2. A dental instrument holder according to claim 1, wherein
   the holding plate is circular and the post receiving aperture is centrally situated in the holding plate.

3. A dental instrument holder according to claim 1, further including
   6. means for preventing rotation of the holding plate relative to the base plate.

* * * * *